(12) United States Patent
Villamena et al.

(10) Patent No.: US 7,598,400 B2
(45) Date of Patent: Oct. 6, 2009

(54) AMPO SPIN TRAPS

(75) Inventors: Frederick Villamena, Columbus, OH (US); Christopher M. Hadad, Dublin, OH (US); Jay L. Zweier, Blacklick, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 99 days.

(21) Appl. No.: 11/286,682

(22) Filed: Nov. 23, 2005

(65) Prior Publication Data

US 2006/0276530 A1 Dec. 7, 2006

Related U.S. Application Data

(60) Provisional application No. 60/630,418, filed on Nov. 23, 2004.

(51) Int. Cl.
C07D 207/22 (2006.01)
(52) U.S. Cl. .................................................. 548/537
(58) Field of Classification Search .................. 548/537
See application file for complete search history.

(56) References Cited

OTHER PUBLICATIONS

Alderson et al. (J. Chem. Soc. Perk. Trans. I, 1976, 1955-60).*
Stolze et al. (Biol. Chem., v. 384, p. 493-500, 2003).*
Villamena et al. (J. Org. Chem., v69, No. 23, p. 7994-8004 (2004)).*
Alderson et al., "Experiments towards the synthesis of corrins. Part XIV.1 Oxidative Decarboxylation of 1-Hydroxypyrrolidine-2-carboxylic acids and oxidation of some Δ1-pyrroline 1-oxides by hypobromite", J Chem Soc, Perkin Trans, 1, 1976, 1955-1960.
Bonnett et al., "Experiments towards the synthesis of corrins. Part II. The preparation and reactions of Δ1-pyrroline 1-oxides", J Chem Soc, 1959, pp. 2094-2102.
Chalier et al., "5-Diisopropoxyphosphoryl-5-methyl-a-pyrroline N-oxide, DIPPMPO, a crystalline analog of the nitrone DEPMPO: synthesis and spin trapping properties", J Chem Soc, Perkin Trans, 2, pp. 2110-2117, 2002.
Chignell, C.F., "Spin trapping studies of photochemical reactions", Pure & Appl Chem, vol. 62, No. 2, pp. 301-305, 1990.
Frejaville et al., "5-(Diethoxyphosphoryl)-5-methyl-1-pyrroline N-Oxide: A new efficient phosphorylated nitrone for the in vitro and the in vivo spin trapping of oxygen-centered radicals", J Med Chem, 38, pp. 258-265, 1995.
Liu et al., "Evaluation of DEPMPO as a spin trapping agent in biological systems", Free Radical Biol. & Medicine, vol. 26, Nos. 5/6, pp. 714-721, 1999.
Olive et al "2-Ethoxycarbonyl-2-methyl-3,4-dihydro-2H-pyrrole-1-oxide: Evaulation of the spin trapping properties" Free Radical Biol & Medicine, vol. 28, No. 3, pp. 403-408, 2000.

Rosen et al., "Influence of conformation on the EPR spectrum of 5,5-dimethyl-1-hydroperoxy-2-pyrrolidinyloxyl: a spin trapped adduct of superoxide", J Org Chem, 69, pp. 1321-1330, 2004.
Stolze et al., "Spin adducts of superoxide, alkoxyl, and lipid-derived radicals with EMPO and its derivatives", Biol Chem, vol. 383, pp. 813-820, May 2002.
Stolze et al., "Synthesis and characterization of EMPO-derived 5,5-disubstituted 1-pyrroline N-oxides as spin traps forming exceptionally stable superoxide spin adducts", Biol Chem, vol. 384, pp. 493,500, Mar. 2003.
Stolze et al., "Spin Trapping of lipid radicals with DEPMPO-derived spin traps: Detection of superoxide, aklyl and alkoxyl radicals in aqueous and lipid phase", Free Radical Biol & Medicine, vol. 29, No. 10, pp. 1005-1014, 2000.
Tsai et al., "Esters of 5-carboxyl-5-methyl-1-pyrroline N-oxide: A family of spin traps for superoxide", J Org Chem, 68, pp. 7811-7817, 2003.
Turner, III et al., "Spin trapping of superoxide and hydroxyl radicals with substituted pyrroline 1-oxides", J Med Chem, 29, pp. 2439-2444, 1986.
Villamena et al., "Superoxide radical trapping and spin adduct decay of 5-tert-butoxycarbonyl-5-methyl-1-pyrroline N-oxide (BoxMPO†): kinetics and theoretical analysis" J Chem Soc, Perkin Trans, 2, pp. 1340-1344, 2002.
Zhang et al., "Detection of superoxide anion using an isotopically labeled nitrone spin trap: potential biological applications", FEBS Letters, 473, pp. 58-62, 2000.
Zhao et al., "Synthesis and biochemical application of a solid cyclic nitrone spin trap: a relatively superior trap for detecting superoxide anions and glutathiyl radicals", Free Radical Biology & Medicine, vol. 31, No. 5, pp. 599-606, 2001.
Spin Trapping, one page, IUPAC Compendium of Chemical Terminology, 2nd Edition, 1997, 1994, 66, 1166.

* cited by examiner

*Primary Examiner*—Rebecca L Anderson
*Assistant Examiner*—Robert Havlin
(74) *Attorney, Agent, or Firm*—Calfee, Halter and Griswold LLP

(57) ABSTRACT

Provided are spin traps for the study of radical formation in vivo or in vitro. 5-carbamoyl-5-methyl-1-pyrroline N-oxide (AMPO) and 2-amino-5-carbamoyl-5-methyl-1-pyrroline N-oxide ($NH_2$-AMPO), have the following structures, respectively:

as well as salts thereof.

8 Claims, 17 Drawing Sheets

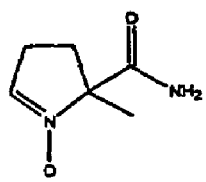
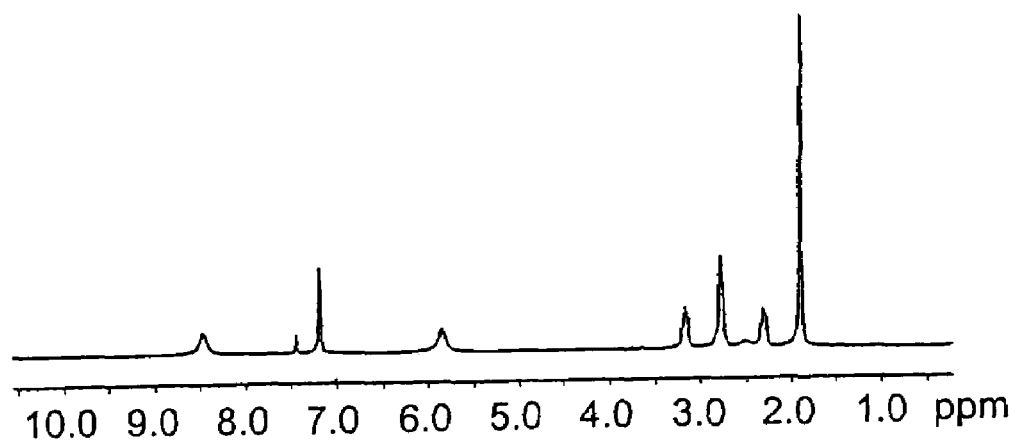
Figure 1. 400 MHz $^1$H-NMR spectrum of AMPO in $CDCl_3$.

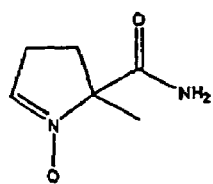
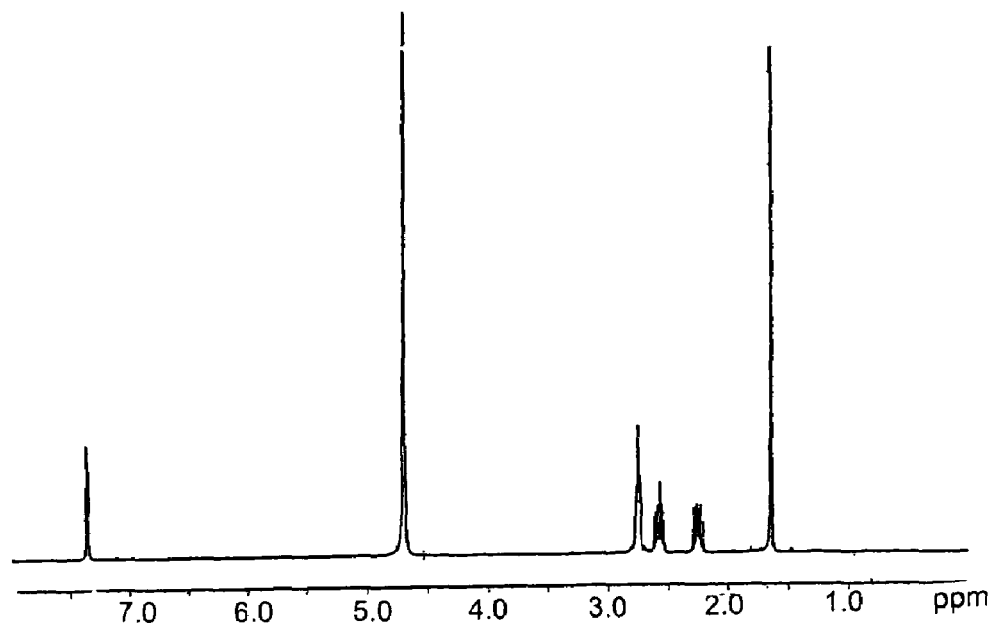
Figure 2. 400 MHz $^1$H-NMR spectrum of AMPO in $D_2O$.

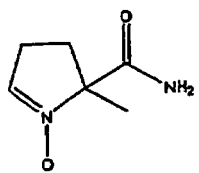
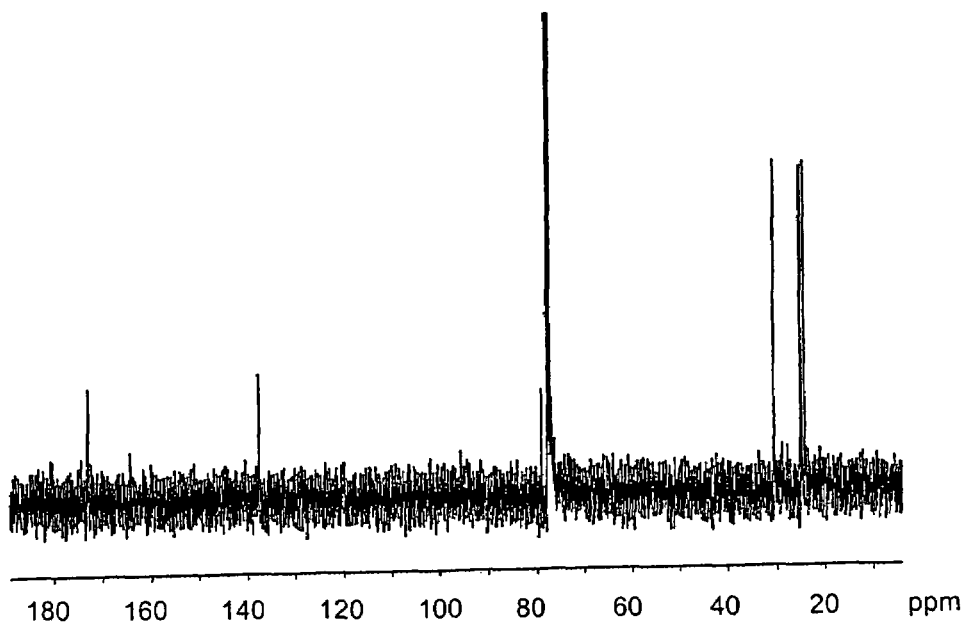
Figure 3. 100 MHz $^{13}$C-NMR spectrum of AMPO in CDCl$_3$.

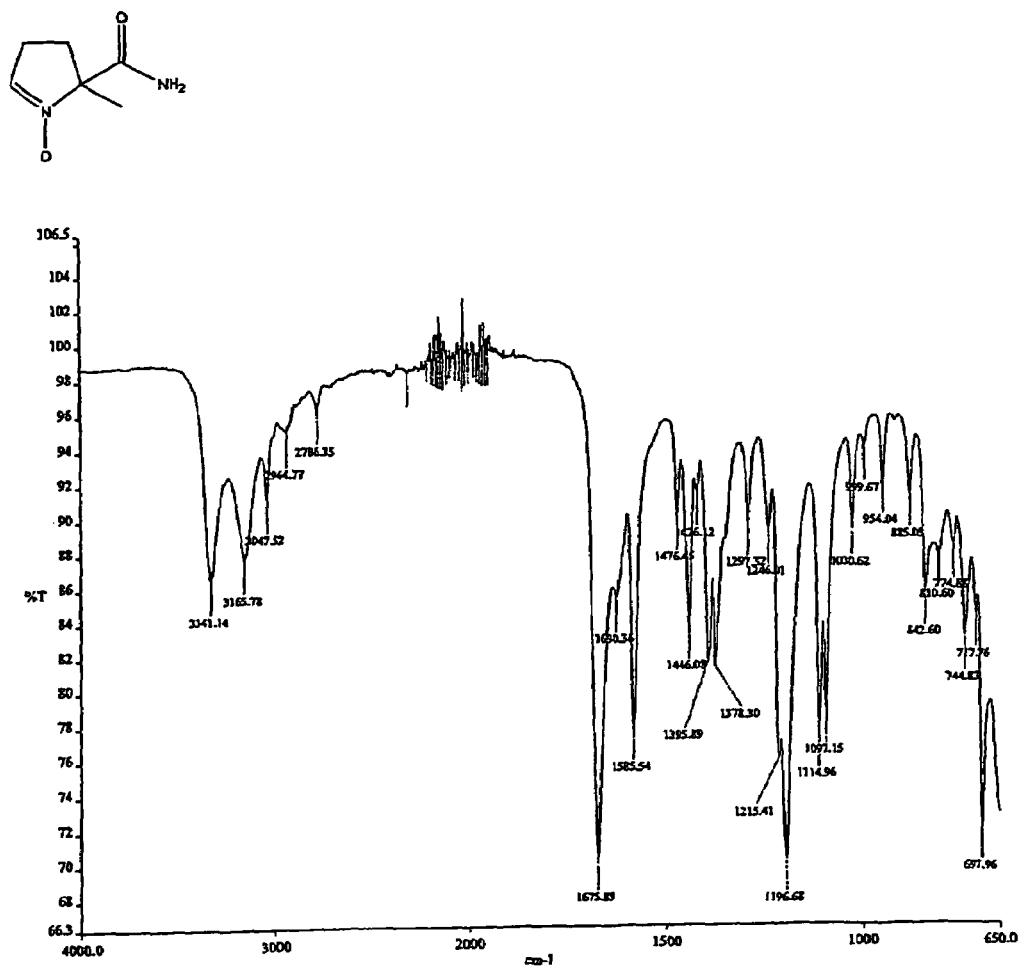
Figure 4. Neat FT-IR spectrum of AMPO.

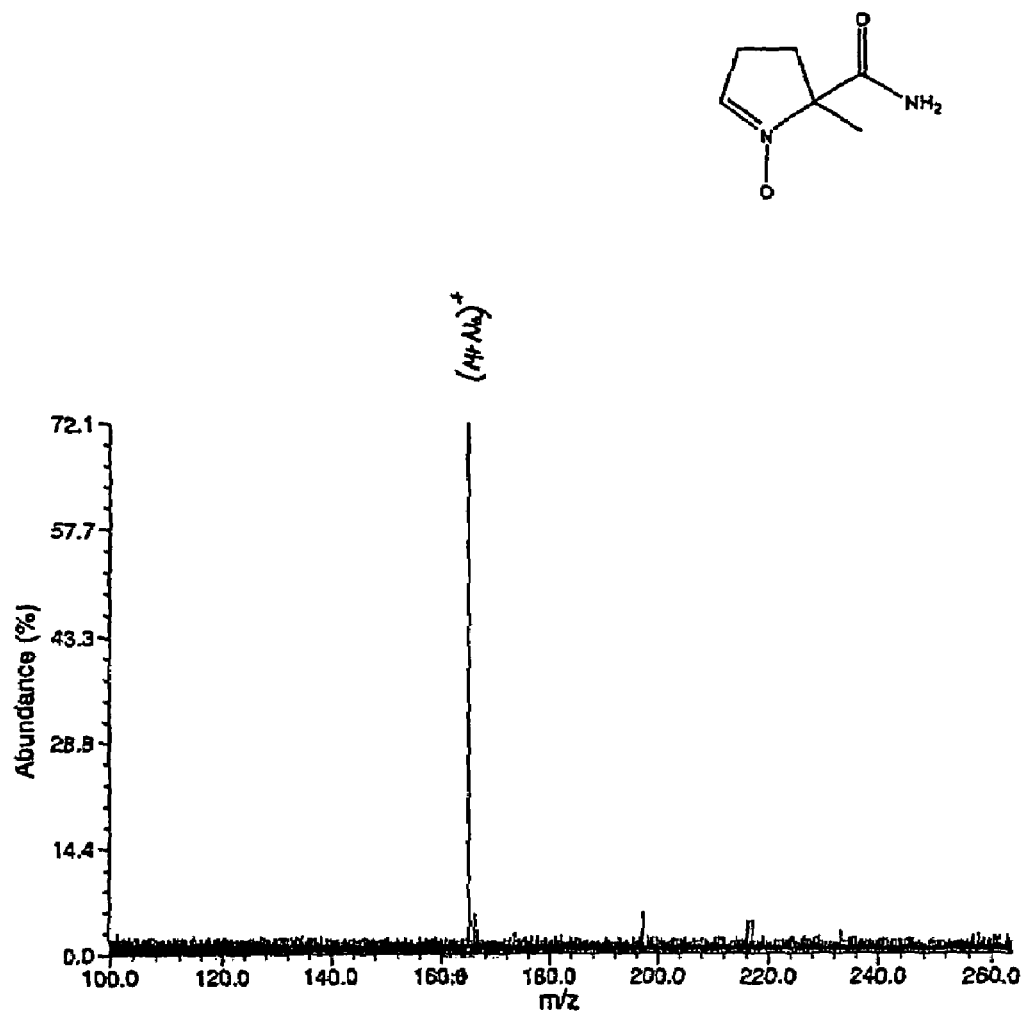
Figure 5. ESI-Mass Spectrum of AMPO.

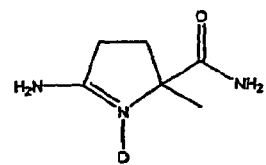
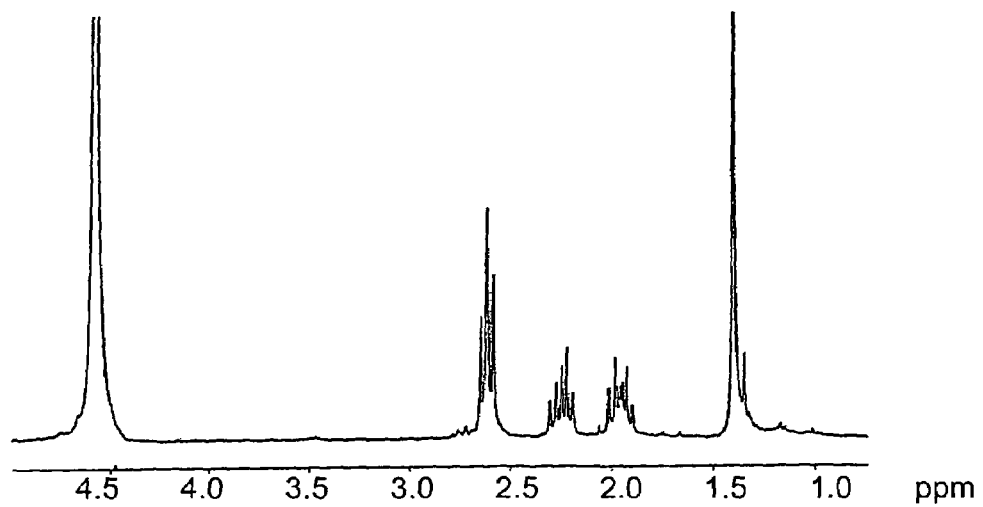
Figure 6. 400 MHz $^1$H-NMR spectrum of $NH_2$-AMPO in $D_2O$.

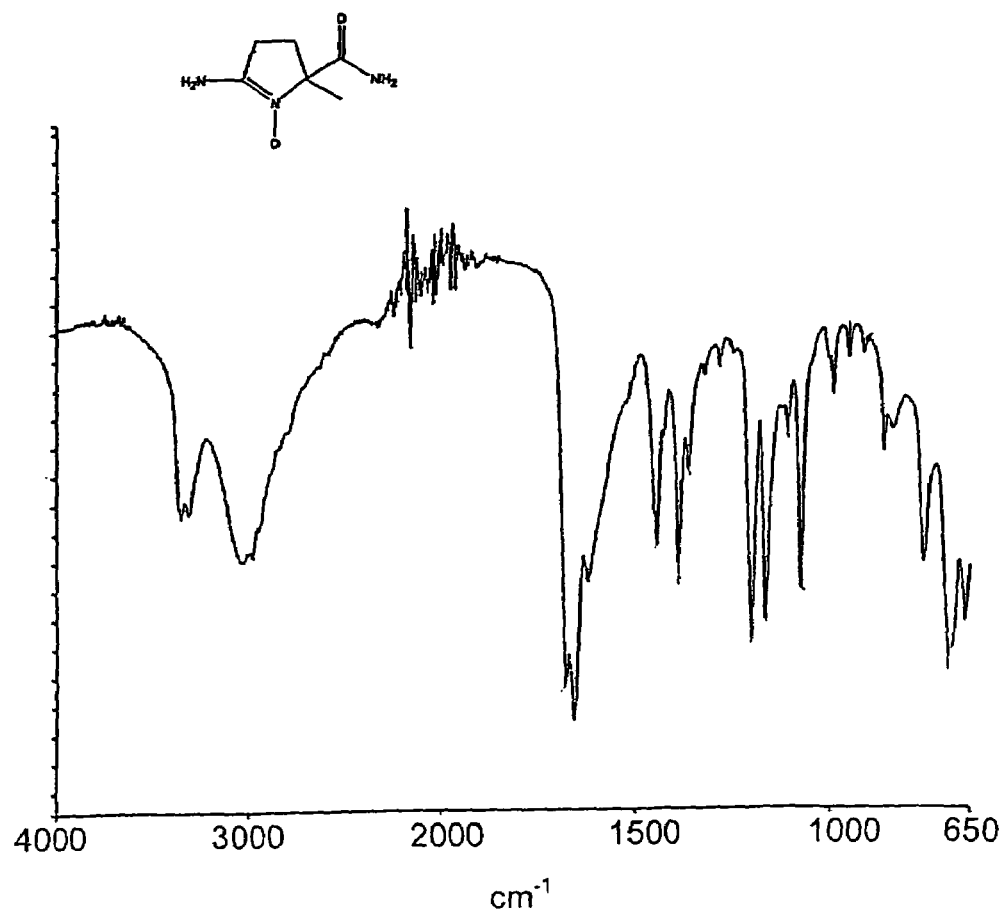
Figure 7. Neat FT-IR spectrum of NH₂-AMPO.

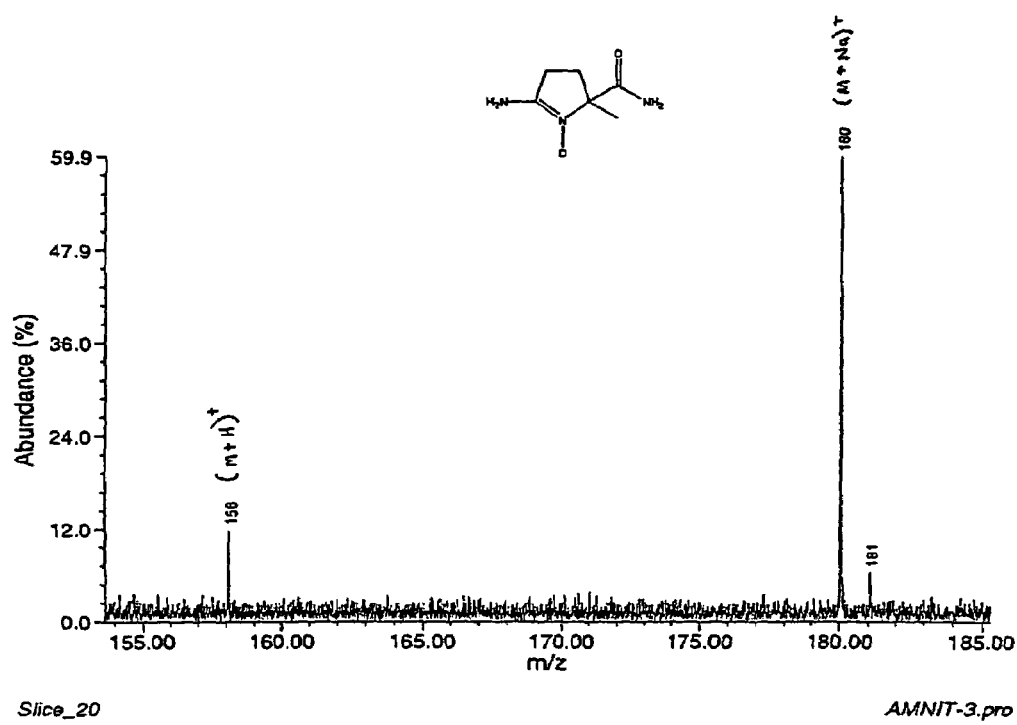
Figure 8. ESI-Mass Spectrum of $NH_2$-AMPO. The $(C_6H_{11}N_3O_2H)^+$ peak has a difference of +6.6 ppm compared to the exact mass, while that of $(C_6H_{11}N_3O_2Na)^+$ has <-1.0 ppm difference.

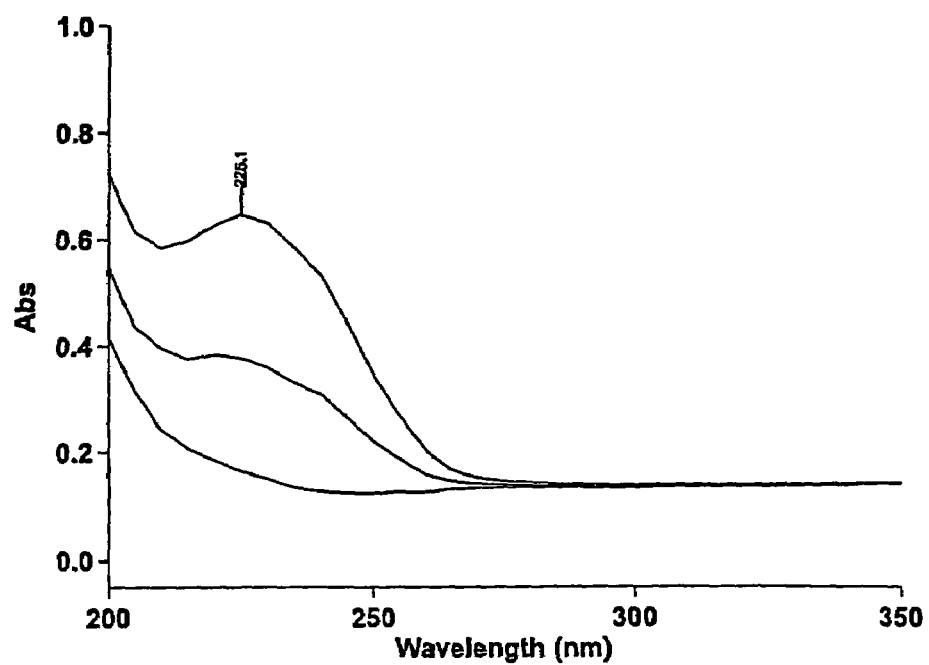
Figure 9. UV-Vis spectrum of 0, 60 and 90 μM NH$_2$-AMPO.

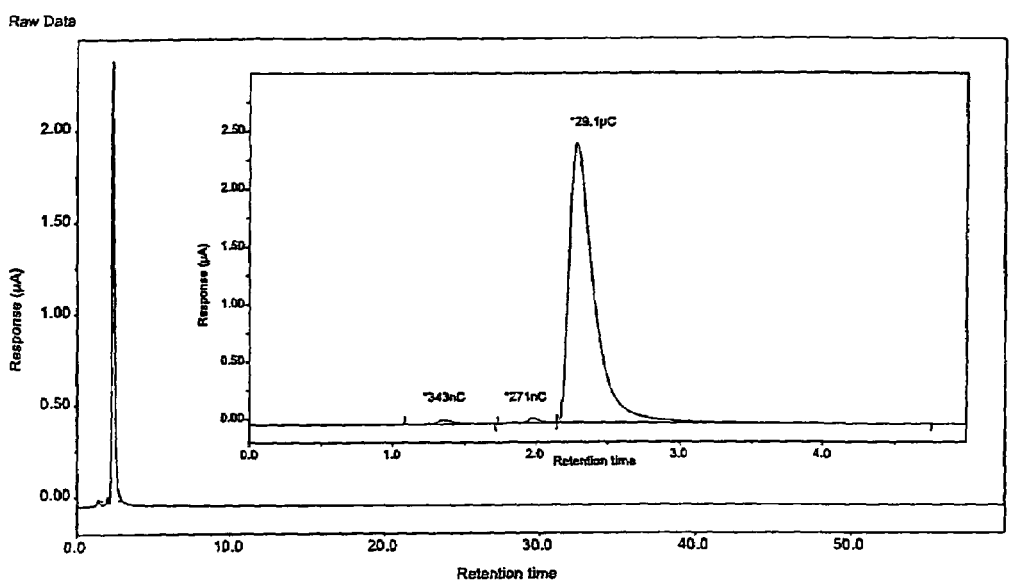
Figure 10. High performance liquid chromatogram of $NH_2$-AMPO. Condition: Stationary phase: C18 column (4.6 mm x 25 cm) with particle size of 5 μm; flow rate = 1.2 mL/min; Solvent: 50:50 (acetonitrile/phosphate-buffer pH 7.4); Detector: UV 230 nm (black line) and 270 nm (green line). Inset: Total integration of all the peaks showing about 2% of 230 nm absorbing impurities.

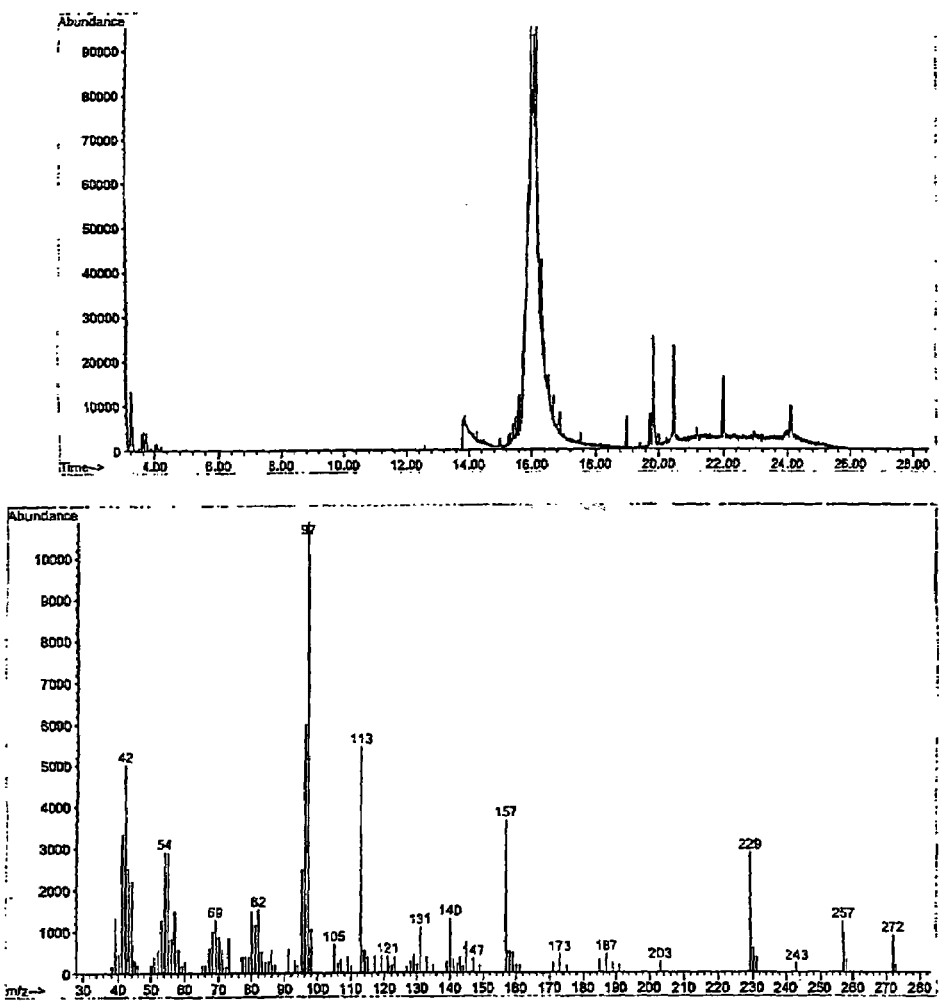
Figure 11. GC-MS chromatogram (top) and spectrum (bottom) of $NH_2$-AMPO. The compound $NH_2$-AMPO has retention time of 16.06 min with a molecular ion peak of 157 m/z.

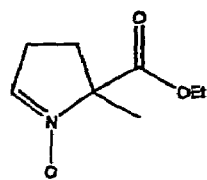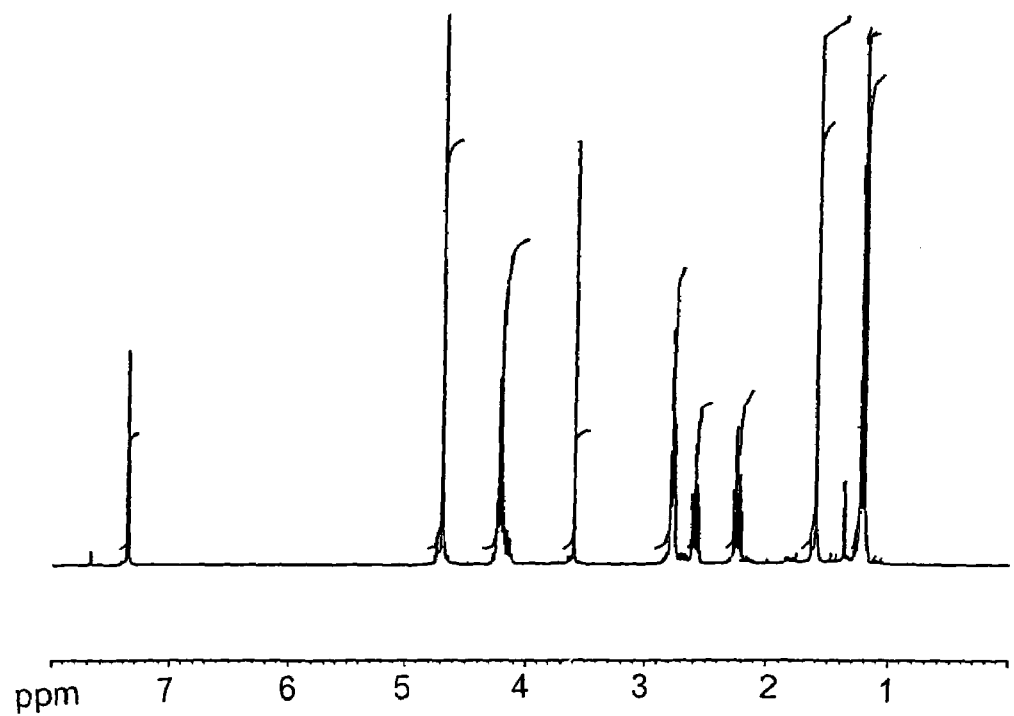
Figure 12. 400 MHz $^1$H-NMR spectrum of EMPO in D$_2$O.

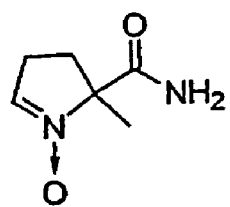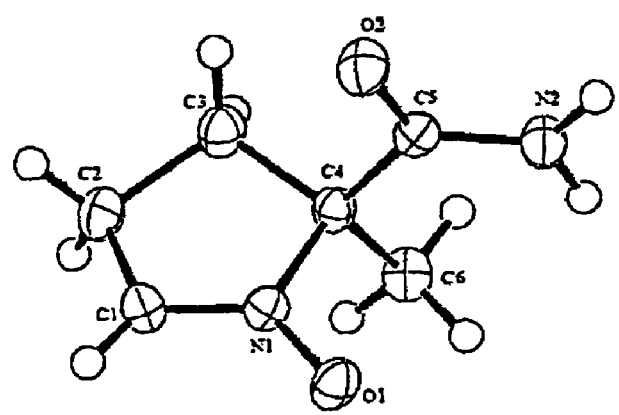
Figure 16

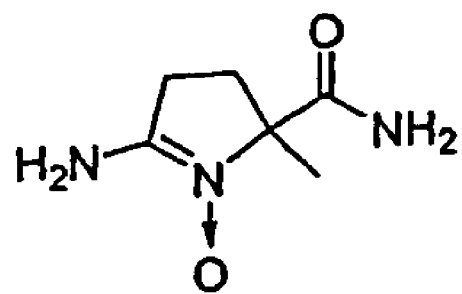
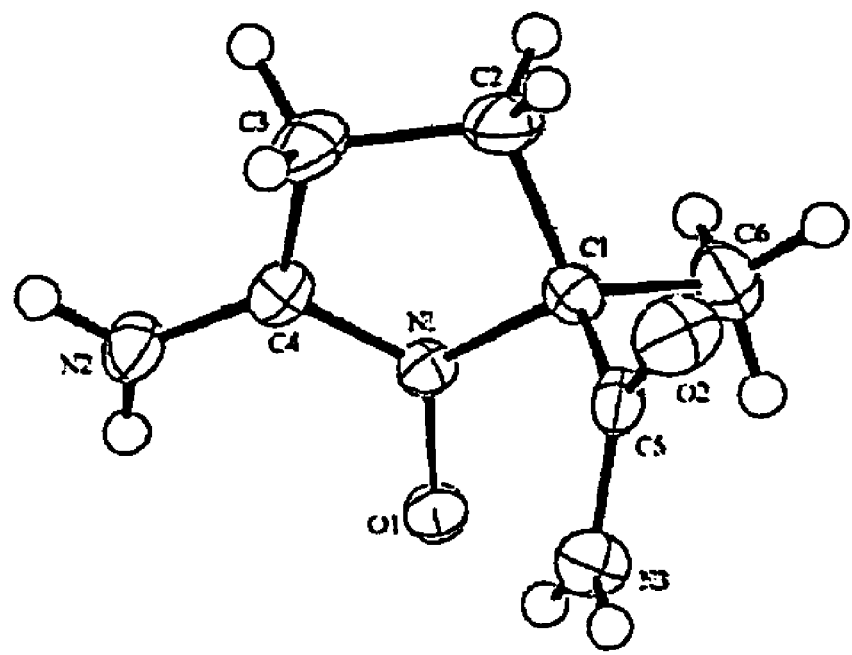
Figure 17

AMPO SPIN TRAPS

CROSS-REFERENCE TO RELATED APPLICATIONS

This application claims priority to U.S. Provisional Patent Application No. 60/630,418 entitled AMPO SPIN TRAPS and filed Nov. 23, 2004, the entirety of which is incorporated herein by reference.

BACKGROUND OF THE INVENTION

Spin traps were originally used to measure free radical activity because they are able to react with free radicals both in vitro and in vivo and can be measured by a number of different techniques, including ESR and NMR. Originally used to measure the efficacy of other anti-oxidants, spin traps have since been recognized that spin traps themselves may be an important tool in treating a variety of conditions, including inflammatory and degenerative age-related diseases.

SUMMARY OF THE INVENTION

Provided are 5-carbamoyl-5-methyl-1-pyrroline N-oxide (AMPO) and 2-amino-5-carbamoyl-5-methyl-1-pyrroline N-oxide ($NH_2$-AMPO), which have the following structures, respectively:

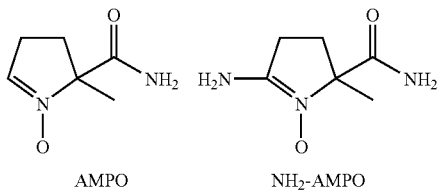

AMPO          $NH_2$-AMPO as well as salts thereof. In some embodiments, the methyl group may be replaced by another group, such as halo or substituted or unsubstituted straight, branched or cyclic alkyl, provided that the compound is still suitable as a spin trap.

The compounds described herein are useful to study radical formation, including but not limited to hydroxyl, superoxide, C-centered, sulfite, and tert-butoxyl radicals. The compounds described herein are particularly useful for studying radical formation in aqueous solutions both in vitro and in vivo. In some embodiments, radicals may be detected by ESR spectroscopy.

BRIEF DESCRIPTION OF THE DRAWINGS

FIG. 1. 400 MHz $^1$H-NMR spectrum of AMPO in $CDCl_3$.
FIG. 2. 400 MHz $^1$H-NMR spectrum of AMPO in $D_2O$.
FIG. 3. 100 MHz $^{13}$C-NMR spectrum of AMPO in $CDCl_3$.
FIG. 4. Neat FT-IR spectrum of AMPO.
FIG. 5. ESI-Mass Spectrum of AMPO.
FIG. 6. 400 MHz $^1$H-NMR spectrum of $NH_2$-AMPO in $D_2O$.
FIG. 7. Neat FT-IR spectrum of $NH_2$-AMPO.
FIG. 8. ESI-Mass Spectrum of $NH_2$-AMPO. The $(C_6H_{11}N_3O_2H)^+$ peak has a difference of +6.6 ppm compared to the exact mass, while that of $(C_6H_{11}N_3O_2Na)^+$ has <−1.0 ppm difference.
FIG. 9. UV-Vis spectrum of 0, 60 and 90 μM $NH_2$-AMPO.
FIG. 10. High performance liquid chromatogram of $NH_2$-AMPO. Condition: Stationary phase: C18 column (4.6 mm×25 cm) with particle size of 5 μm; flow rate=1.2 mL/min; Solvent: 50:50 (acetonitrile/phosphate-buffer pH 7.4); Detector: UV 230 nm (black line) and 270 nm (green line). Inset: Total integration of all the peaks showing about 2% of 230 nm absorbing impurities.
FIG. 11. GC-MS chromatogram (top) and spectrum (bottom) of $NH_2$-AMPO. The compound $NH_2$-AMPO has retention time of 16.06 min with a molecular ion peak of 157 m/z.
FIG. 12. 400 MHz 1H-NMR spectrum of EMPO in $D_2O$.
FIG. 16. A view of the X-ray structure of AMPO. The non-hydrogen atoms are drawn with 50% probability displacement ellipsoids. The hydrogen atoms are drawn with an arbitrary radius.
FIG. 17. A view of the X-ray structure of $NH_2$-AMPO. The non-hydrogen atoms are drawn with 50% probability displacement ellipsoids. The hydrogen atoms are drawn with an arbitrary radius.

DETAILED DESCRIPTION OF THE INVENTION

Figure 13:
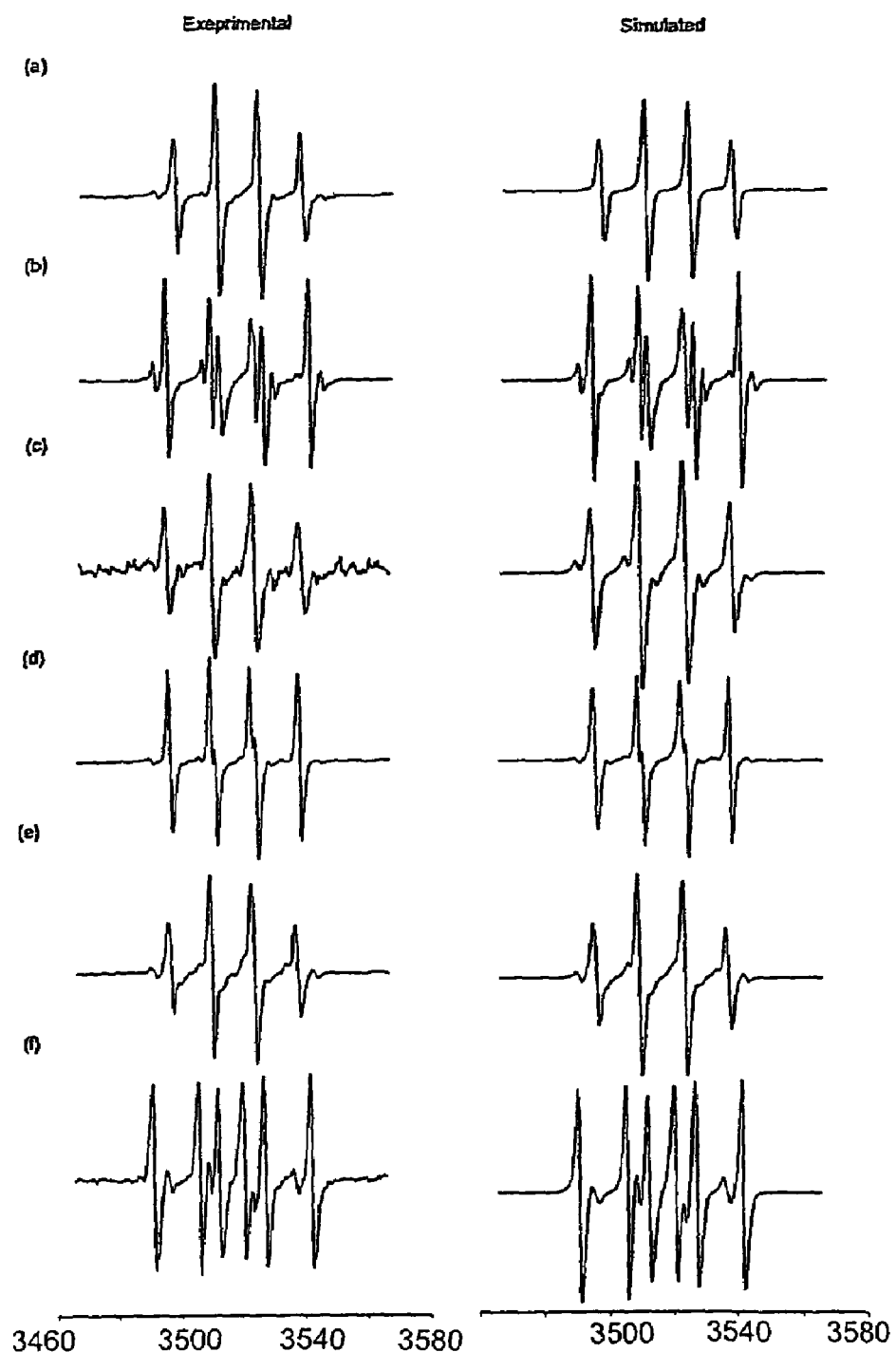
FIG. 13. Experimental (left) and simulated (right) EPR spectra of AMPO radical adducts with (a) .OH; (b) $CO_2^{·−}$; (c) GS.; (d) $SO_3^{·−}$; (e) tert-BuO. and (f) $CH_3$.CHOH. See experimental methods of radical generation and spectrometer settings.
Figure 14:
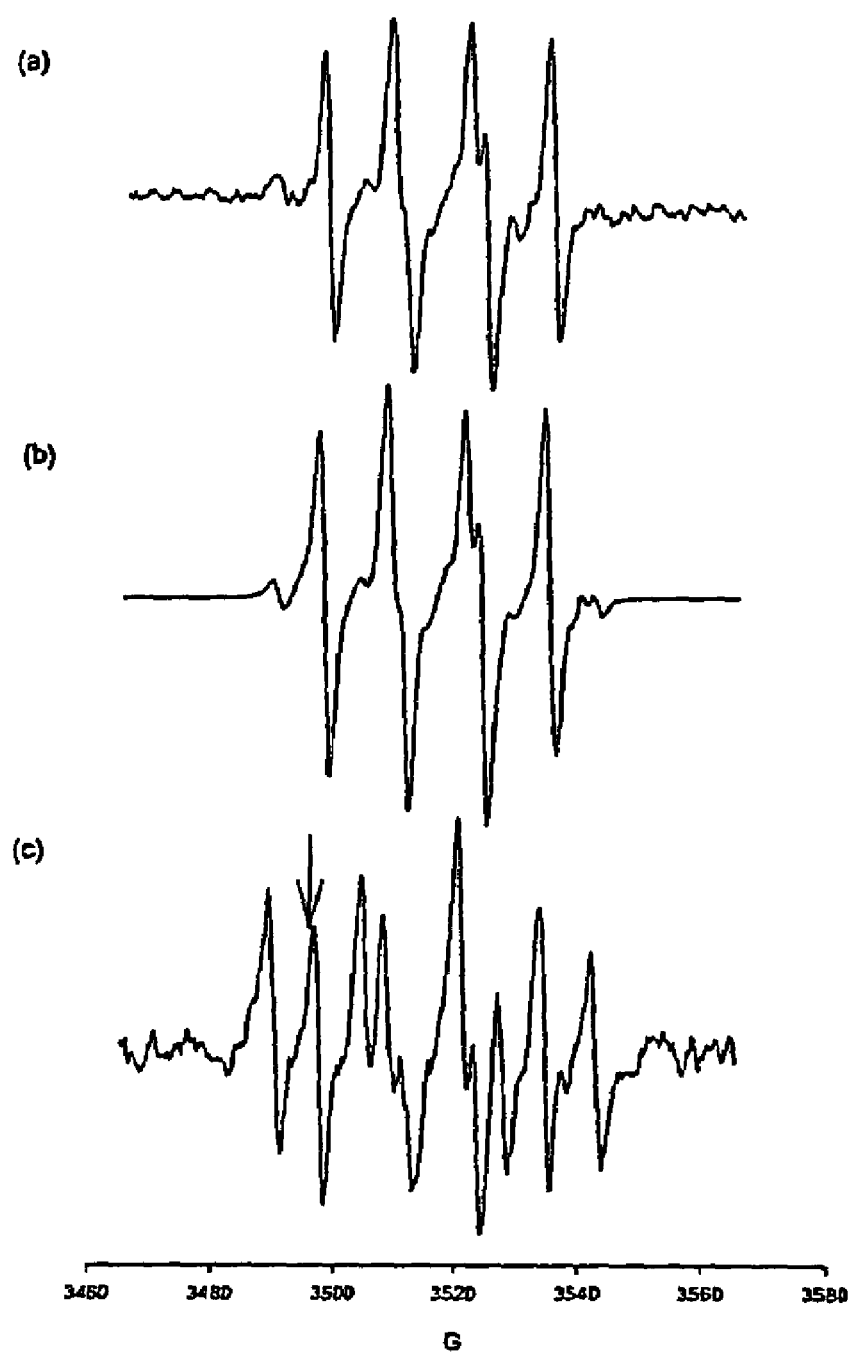
FIG. 14. EPR spectral profile of AMPO-$O_2$H (a) generated by xanthine-xanthine oxidase; (b) simulated spectrum based on the parameters described in Table 2; (c) generated by light-riboflavin system (note the significant contribution from a C-centered adduct). See experimental methods for spectrometer settings. Arrow indicates the peak being monitored during kinetic studies.
Figure 15:
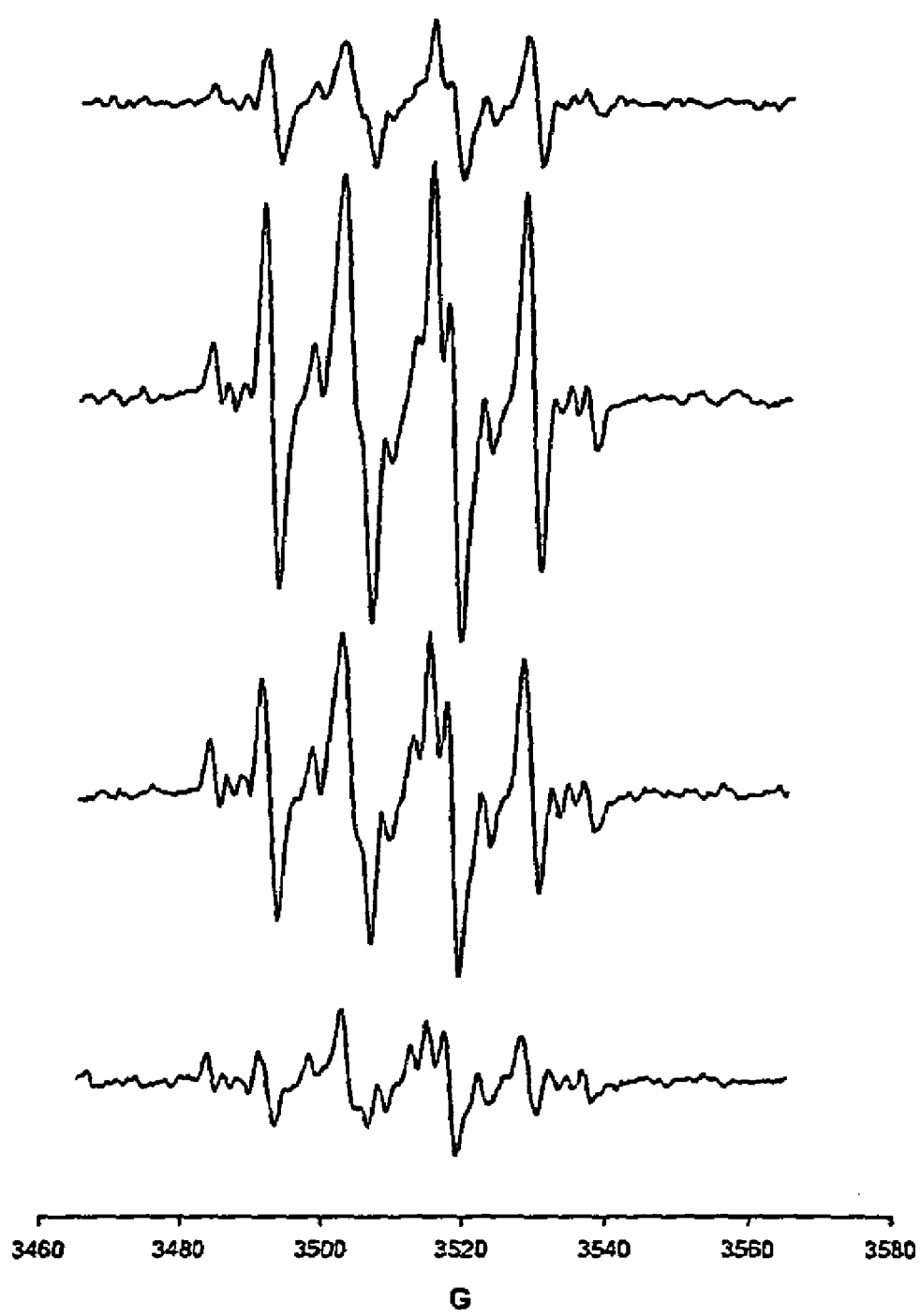
FIG. 15. Superoxide adduct formation by 25 mM AMPO using PMA-activated neutrophiles. (Top to bottom): 2, 10, 30, 60 min after the addition of PMA.

Provided are new spin traps and methods of making and using the same. The spin traps described herein include the nitrone 5-carbamoyl-5-methyl-1-pyrroline N-oxide (AMPO), the amido nitrone compound 2-amino-5-carbamoyl-5-methyl-1-pyrroline N-oxide ($NH_2$-AMPO) and derivatives thereof. Spin trapping by AMPO of hydroxyl, superoxide, C-centered, sulfite, and tert-butoxyl radicals has been demonstrated by electron paramagnetic resonance (EPR) spectroscopy, making these compounds useful for the study of radical production in aqueous systems.

The nitrone 5-carbamoyl-5-methyl-1-pyrroline N-oxide (AMPO) was successfully synthesized and characterized. Spin trapping by AMPO of hydroxyl, superoxide, C-centered, sulfite, and tert-butoxyl radicals has been demonstrated for the first time by electron paramagnetic resonance (EPR) spectroscopy. Resulting spin adducts for each of these radicals gave unique spectral profiles. Rate of superoxide radical trapping was obtained by competitive trapping by AMPO versus DEPMPO and gave kAMPO=38 $M^{−1}$ $s^{−1}$ (based on kDEPMPO=58 $M^{−1}$ $s^{−1}$) comparable to that of EMPO kEMPO=44 $M^{−1}$ $s^{−1}$. The half-life of AMPO-$O_2$ adduct is about $t_{1/2}$~10 minutes similar to that observed from EMPO but significantly shorter than that of DEPMPO-$O_2$ adduct $t_{1/2}$~16 minutes. Theoretical analyses using density functional theory calculations at the B3LYP/6-31=G**/B3LYP6-31G* level were performed on AMPO and its corresponding suproxide product. Calculations predicted the presence of intramolecular H-bonding in both AMPO and its superoxide adduct, and these interactions were further confirmed by an X-ray structure (in the case of AMPO) of a novel and the amido nitrone compound 2-amino-5-carbamoyl-5-methyl-1-pyrroline N-oxide ($NH_2$-AMPO). The thermodynamic quantities for superoxide radical trapping by various nitrones have been found to predict favorable formation of certain isomers. The measured partition coefficient in an n-octanol/buffer system of AMPO gave a comparable value to those of DMPO and DEPMPO. This study demonstrates the suitability of AMPO nitrone as spin trap to study radical production in aqueous systems.

These new compounds are useful both to study radical production in aqueous systems, both in vitro and in vivo. Additionally, these compounds may be useful in the treatment of inflammatory conditions and chronic degenerative diseases of aging. Some conditions that these compounds may be useful in treating include but are not limited to AIDS, arthritis, arteriosclerosis, Alzheimer's disease and other pro-inflammatory disease conditions.

General Experimental Procedure for the Preparation of AMPO and $NH_2$-AMPO All chemicals were purchased and used without further purification. Elemental analysis was performed by a commercial analytical service company. $^1$H-NMR and $^{13}$C-NMR measurements were performed on a 400 MHz and 100 MHz spectrometer. FT-IR measurements were performed using neat samples.

5-Ethoxycarbonyl-5-methyl-1-pyrroline N-oxide (EMPO). EMPO was synthesized according to the method described previously by Bonnett, et al.[1] EMPO: clear liquid; $^1$H NMR (400 MHz, $D_2O$) δ 1.23 (3 H, t, O—$CH_2$), 1.61 (3 H, s, C(5)Me), 2.23-2.28 and 2.56-2.63 (2 H, m, C(4)H), 2.76-2.81 (2 H, m, C(3)H), 4.19-4.25 (2H, q, O—$CH_2CH_3$), 7.37 (1H, t, C(2)H). IR (Neat film) 1737 (C=O), 1583 (C=N), 1214 (N—O).

5-Carbamoyl-5-methyl-1-pyrroline N-oxide (AMPO). AMPO was prepared from EMPO based on the procedure described previously with minor modification.[2] A solution of 0.5 g of EMPO was mixed with 10 mL of concentrated ammonium hydroxide in a sealed tube for 5 days at room temperature with shaking. The mixture was rotary evaporated to yield a viscous dark oil and passed through a silica gel column (200-400 mesh 60 Å) twice using methanol-ethyl acetate (30:70) as solvent. White crystalline product was obtained (0.10 g, 24%), mp. 134-135° C. (lit. 137° C.)., (corrected using 3,4 dimethoxybenzoic acid, m.p., 180° C. and urea, m.p., 135° C.). $^1$H NMR (400 MHz, $D_2O$) δ 1.64 (3 H, s, C(5)Me), 2.21-2.29 and 2.54-2.61 (2 H, m, C(4)H), 2.73-2.73 (2 H, m, C(3)H), 7.36 (1 H, t, C(2)H). $^1$H NMR (400 MHz, $CDCl_3$) 1.90 (3 H, s, C(5)Me), 2.27-2.34 and 3.14-3.20 (2 H, m, C(4)H), 2.79 (2 H, m, C(3)H), 7.19 (1 H, t, C(2)H), 5.85 and 8.46 (2 H, br, $NH_2$). $^{13}$C NMR (100 MHz, $CDCl_3$) δ 24.2 (s, —$CH_3$), 25.0 (s, C-3), 30.5 (s, C-4), 79.1 (C-5), 137.4 (C-2), 172.9 (—C=O). IR (Neat film) 1676 (C=O), 1585 (C=N), 1215 (N—O). ESI-MS calcd for $C_6H_{10}N_2O_2Na^+$ m/z 165.0634, found 165.0637 amu. Anal. Calcd. for $C_6H_{10}N_2O_2$: C, 50.81; H, 7.23; N, 19.14. Found: C, 50.61; H, 7.25; N, 19.31.

2-Amino-5-carbamoyl-5-methyl-1-pyrroline N-oxide ($NH_2$-AMPO). $NH_2$-AMPO was prepared using the procedure described previously[39] using cyanide as catalyst for the aminolysis of esters. A solution of 100 mg (0.584 mmol) of EMPO in 25 mL of ca. 12N $NH_3$ in MeOH and 28 mg (0.058 mmol) of NaCN was heated to 60° C. in a sealed tube for 40 hr. The solvent was evaporated and the residue was redissolved in $CH_2Cl_2$. The organic phase was extracted with minimal amount of water and dried over $MgSO_4$. Evaporation of the solvent gave mixture of AMPO and $NH_2$-AMPO. The crude product was purified by column chromatography using silica gel and methanol-ethyl acetate (30:70) as solvent. The product was further purified twice by column chromatography using EtOH as solvent which afforded $NH_2$-AMPO (5 mg), mp. >200 (dec). $^1$H NMR (400 MHz, $D_2O$, 4.58 ppm) δ 1.40 (3 H, s, C(5)Me), 1.90-2.06 and 2.22-2.35 (2 H, m, C(4)H), 2.59-2.65 (2 H, m, C(3)H). IR (Neat film) 3346 and 1661 (N—H), 1682 (C=O), 1627 (C=N), 1201 (N—O). ESI-MS calcd for $C_6H_{11}N_3O_2Na^+$ m/z 180.0749, found 180.0743 amu.

Miscellaneous Spin Trapping Studies Fenton reaction system. A 50 μL 0.1 M phosphate buffer solution containing 30 mM AMPO, 1% $H_2O_2$ and 65 mM $FeSO_4$ was transferred to a 50 μL capillary tube and EPR spectrum of the hydroxyl adduct was recorded over 5 min time period.

Trapping of $SO_3^{•-}$, $CO_2^{•-}$ and $CH_3$.CHOH radicals. 50 μL 0.1 M phosphate buffer solution containing 30 mM AMPO, 1% $H_2O_2$ and 100 mM of the respective radical source $NaHCO_2$, $Na_2SO_3$, or ethanol with 65 mM freshly prepared $FeSO_4$. The mixture was then transferred to 50 μL capillary tube and EPR spectrum of the adduct was recorded over a 5 min time period.

Trapping of GS. and t-BuO. radicals. 50 μL 0.1 M phosphate buffer solution containing 30 mM AMPO and 100 mM GSSG or $(CH_3)_3CO$—$OC(CH_3)_3$. The mixture was then transferred to 50 μL capillary tube and the radicals were generated by UV photolysis. EPR spectrum of the adduct was recorded over a 5 min time period.

Trapping of $O_2^{•-}$. Typical $O_2^{•-}$ trapping experiments utilized the riboflavin-light system as described in the Kinetics section. An alternative $O_2^{•-}$ generating system used a solution of 0.4 mM xanthine and 0.5 unit/mL xanthine oxidase, or 10 nM PMA and 8×105 neutrophil cells in 25 mM AMPO. Spectra were acquired over a period of 15 min.

TABLE 1

EPR parameters of simulated radical adducts of AMPO[a]

| Radicals | Generating system | Diastereomers (%) | Hyperfine coupling constants (G) | | |
|---|---|---|---|---|---|
| | | | $a_N$ | $a_H^β$ | $a_H^γ$ |
| $O_2^{•-}$ | HX/XO | 80 | 13.0 | 10.8 | |
| | | 20 | 13.1 | 12.5 | 1.75 |
| •OH | $Fe^{2+}$—$H_2O_2$ | 69 | 14.0 | 13.5 | |
| | | 31 | 14.0 | 12.5 | |
| $CO_2^{•-b}$ | $Fe^{2+}$—$H_2O_2$—$NaHCO_2$ | 47 | 14.25 | 18.15 | |
| | | 53 | 14.53 | 16.48 | |
| $SO_3^{•-c}$ | $Fe^{2+}$—$H_2O_2$—$Na_2SO_3$ | 46 | 13.47 | 15.93 | |
| | | 54 | 13.47 | 14.67 | |
| $CH_3$•CHOH[d] | $Fe^{2+}$—$H_2O_2$—EtOH | 100 | 14.8 | 21.4 | |
| $(CH_3)_3CO•$[e] | $(CH_3)_3COOC(CH_3)_3$—uv | 56 | 14.19 | 13.64 | |
| | | 44 | 13.85 | 12.79 | |

TABLE 1-continued

EPR parameters of simulated radical adducts of AMPO[a]

| Radicals | Generating system | Diastereomers (%) | Hyperfine coupling constants (G) | | |
|---|---|---|---|---|---|
| | | | $a_N$ | $a_H^\beta$ | $a_H^\gamma$ |
| GS•[f] | GSSG-uv | 90 | 14.26 | 14.96 | |
| | | 10 | 14.39 | 12.06 | |

[a]Based on the simulation program by Rockenbauer, A., et al.35
Simulated spectrum contains:
[b]19% C-centered adduct and 12% OH adduct
[c]23% C-centered adduct
[d]13% OH adduct
[e]10% C-centered adduct and 12% OOH-like adduct
[f]12% C-centered adduct X-ray Crystallographic Data For AMPO The data collection crystal of AMPO was a thin colorless plate. Examination of the diffraction pattern on a CCD diffractometer indicated a monoclinic crystal system. All work was done at 200 K. The data collection strategy was set up to measure a quadrant of reciprocal space with a redundancy factor of 3.1, which means that 90% of the reflections were measured at least 3.1 times. A combination of phi and omega scans with a frame width of 2.0° was used. Data integration was done with Denzo[7] and scaling and merging of the data was done with Scalepack[7]. Merging the data and averaging the symmetry equivalent reflections resulted in an Rint value of 0.044.

The structure was solved by the direct methods in SHELXS-86[8]. Full-matrix least-squares refinements based on $F^2$ were performed in SHELXL-93[9].

For the methyl group, the hydrogen atoms were added at calculated positions using a riding model with U(H)=1.5 * Ueq(bonded atom). The torsion angle, which defines the orientation of the methyl group about the C—C bond, was refined. The two hydrogen atoms bonded to N(2) were found on a difference map and then refined isotropically. The remaining hydrogen atoms were included in the model at calculated positions using a riding model with U(H)=1.2 * Ueq(attached atom). The final refinement cycle was based on 1173 intensities and 100 variables and resulted in agreement factors of R1(F)=0.060 and wR2($F^2$=0.103). For the subset of data with I>2σ(I), the R1(F) value is 0.040 for 907 reflections. The final difference electron density map contains maximum and minimum peak heights of 0.14 and −0.25 e/Å$^3$. Neutral atom scattering factors were used and include terms for anomalous dispersion[10]. The PLATON program[11] was used to calculate the metrical parameters for the hydrogen bonds.

TABLE 2

Crystallographic Data for AMPO.

| | |
|---|---|
| empirical formula | $C_6H_{10}N_2O_2$ |
| formula weight | 142.16 |
| crystal system | monoclinic |
| space group. Z | P2(1)/c, 4 |
| a (Å) | 10.758(4) |
| b (Å) | 5.764(2) |
| c (Å) | 11.105(5) |
| b (°) | 104.670(10) |
| unit cell volume Å$^3$ | 666.2(5) |
| $\rho_{calc}$ (g cm$^{-3}$) | 1.417 |
| T(K) | 200(2) K |
| wavelength | 0.71073 Å |
| μ(mm$^{-1}$) | 0.108 |
| final R[a] | $R_1 = 0.0401$ |
| | $wR_2 = 0.0950$ |

[a]$R_1 = \Sigma ||F_o| - |F_c||/\Sigma |F_o|$ with I > 2 (I) and $wR_2 = [\Sigma[w(F_o^2 - F_c^2)^2]/\Sigma[w(F_o^2)^2]]^{1/2}$.

X-ray Crystallographic Data For NH$_2$-AMPO The data collection crystal NH$_2$-AMPO was a pale yellow, approximately rectangular plate. Examination of the diffraction pattern on a CCD diffractometer indicated an orthorhombic crystal system. All work was done at 200 K. The data collection strategy was set up to measure an octant of reciprocal space with a redundancy factor of 4.4, which means that 90% of the reflections were measured at least 4.4 times. A combination of phi and omega scans with a frame width of 2.0° was used. Data integration was done with Denzo[12] and scaling and merging of the data was done with Scalepack[12]. Merging the data and averaging the symmetry equivalent reflections resulted in an Rint value of 0.044. The teXsan[56] package indicated the space group to be P2$_1$2$_1$2$_1$.

The structure was solved by direct methods in SHELXS-86[13]. Based on the X-ray data only, it is not possible to determine which enantiomer is present in this structure. Full-matrix least squares refinement based on F were performed in SHELXL-93[14].

For the methyl group, the hydrogen atoms were added at calculated positions using a riding model with U(H)=1.5 * Ueq(bonded atom). The torsion angle, which defines the orientation of the methyl group about the C—C bond, was refined. The hydrogen atoms bonded to nitrogen atoms were refined isotropically. The remaining hydrogen atoms were included in the model at calculated positions using a riding model with U(H)=1.2 * Ueq(attached atom). The final refinement cycle was based on 1709 intensities and 117 variables and resulted in agreement factors of R1(F)=0.059 and wR2 ($F^2$=0.088). For the subset of data with I>2 σ(I), the R1(F) value is 0.040 for 1369 reflections. The final difference electron density map contains maximum and minimum peak heights of 0.16 and −0.17 e/Å$^3$. Neutral atom scattering factors were used and include terms for anomalous dispersion[15].

The PLATON program[16] was used to calculate the metrical parameters for the hydrogen bonds.

All of the hydrogen atoms of the $NH_2$ groups are involved in intra and intermolecular hydrogen bonds.

TABLE 3

Crystallographic Data for $NH_2$-AMPO.

| | |
|---|---|
| empirical formula | $C_6H_{11}N_3O_2$ |
| formula weight | 157.18 |
| crystal system | orthorhombic |
| space group, Z | $P2_1 2_1 2_1$, 4 |
| a (Å) | 7.582(2) |
| b (Å) | 9.269(3) |
| c (Å) | 10.682(3) |
| unit cell volume Å$^3$ | 750.7(4) |
| $\rho_{calc}$(g cm$^{-3}$) | 1.391 |
| T(K) | 200(2) |
| wavelength | 0.71073 Å |
| $\mu$ (mm$^{-1}$) | 0.106 |
| final R$^a$ | $R_1$ = 0.0397 |
| | $wR_2$ = 0.0808 |

$^a R_1 = \Sigma ||F_o| - |F_c||/\Sigma |F_o|$ with $I > 2\sigma(I)$ and $wR_2 = [\Sigma[w(F_o^2 - F_c^2)^2]/\Sigma[w(F_o^2)^2]]^{1/2}$.

Decay Kinetics In a typical decay kinetic study, 50 μL solution containing 25 mM of the nitrone and 100 μM riboflavin was irradiated for 3 min in the cavity. The lowest-field peak decay was monitored as a function of time over a period of 2680 s after the light source was turned off. All data were the average of 3 or more measurements.

TABLE 4

First order approximation half-lives of nitrone-superoxide adducts and partition coefficient of the nitrone spin traps at pH 7.2 and 23° C.

| Spin trap | $k_f/10^{-4}s^{-1}$ | $t_{1/2}$/min$^a$ | ref. | $K_p$ (n-octanol/water)$^b$ |
|---|---|---|---|---|
| AMPO | 14.0 ± 1.2 | 8.3 ± 0.7 | this work | 0.03 |
| EMPO | 11.6 ± 0.5 | 9.9 ± 0.4 | this work | 0.33 |
| | | 8.6, 8.0 | 14,36 | |
| | | 24.6 ± 2.7 | 18 | |
| DEPMPO | 7.5 ± 0.7 | 15.5 ± 1.4 | this work | 0.16 |
| | 8.13 | 14.2 | 16 | |
| DMPO | 129.0 | 0.9 | 16 | 0.06 |

$^a$Based on the first-order rate constant and values are mean average of 3-6 measurements.
$^b$Shaken for 2 hrs at 37° C.

These DMPO-type spin traps include the alkoxyphosphorylated nitrones 5-diethoxyphosphoryl-5-methyl-1-pyrroline N-oxide (DEPMPO)[17-19] and 5-diisopropyloxyphosphoryl-5-methyl-1-pyrroline N-oxide (DIPPMPO)[20], and the alkoxycarbonyl-nitrones, 5-ethoxycarbonyl-5-methyl-1-pyrroline N-oxide (EMPO)[21-24] and 5-butoxycarbonyl-5-methyl-1-pyrroline N-oxide (BocMPO).[24-27]

The examples included herein are for illustration and are not meant to limit the scope of the invention. All articles cited are incorporated herein by reference.

REFERENCES (1) Bonnett, R.; Brown, R. F. C.; Clark, V. M.; Sutherland, I. O.; Todd, A. *J. Chem. Soc.* 1959, 2094-2102.
(2) Alderson, G. W.; Black, D. S.; Clark, V. M.; Todd, L. *J. Chem. Soc., Perkin Trans.* 1 1976, 1955-1960.
(3) Turner, M. J.; Rosen, G. M. *J. Med. Chem.* 1986, 29, 2439-2444.
(4) Tsai, P.; Ichikawa, K.; Mailer, C.; Pou, S.; Halpern, H. J.; Robinson, B. H.; Nielsen, R.; Rosen, G. M. *J. Org. Chem.* 2003, 68, 7811-7817.
(5) Frejaville, C.; Karoui, H.; Tuccio, B.; Le Moigne, F.; Culcasi, M.; Pietri, S.; Lauricella, R.; Tordo, P. *J. Med. Chem.* 1995, 38, 258-265.
(6) Rosen, G. M.; Beselman, A.; Tsai, P.; Pou, S.; Mailer, C.; Ichikawa, K.; Robinson, B. H.; Nielsen, R.; Halpern, H. J.; MacKerell, A. D. *J. Org. Chem.* 2004, 69, 1321-1330.
(7) DENZO: Otwinowski, Z. \& Minor, W., Methods in Enzymology, Vol 276: Macromolecular Crystallography, part A, 307-326, (1997), Carter, Jr., C. W. \& Sweet, R. M., Eds., Academic Press.
(8) SHELXS-86: Sheldrick, G. M., Acta Cryst., (1990), A46, 467-473.
(9) SHELXL-93: Sheldrick, G. M., University of Gottingen, Germany, 1993.
(10) International Tables for Crystallography (1992). Volume C. Dordrecht: Kluwer Academic Publishers.
(11) PLATON: Spek, A. L., J. Appl. Cryst., (2003), 36, 7-13.
(12) DENZO: Otwinowski, Z. \& Minor, W., Methods in Enzymology, Vol 276: Macromolecular Crystallography, part A, 307-326, (1997), Carter, Jr., C. W. \& Sweet, R. M., Eds., Academic Press.
(13) SHELXS-86: Sheldrick, G. M., Acta Cryst., (1990), A46, 467-473.
(14) SHELXL-93: Sheldrick, G. M., University of Gottingen, Germany, 1993.
(15) International Tables for Crystallography (1992). Volume C. Dordrecht: Kluwer Publishers.
(16) PLATON: Spek, A. L., J. Appl. Cryst., (2003), 36, 7-13.
(17) Frejaville, C.; Karoui, H.; Tuccio, B.; Le Moigne, F.; Culcasi, M.; Pietri, S.; Lauricella, R.; Tordo, P. *J. Med. Chem.* 1995, 38, 258-265.
(18) Liu, K. J.; Miyake, M.; Panz, T.; Swartz, H. *Free Rad. Biol. Med.* 1999, 26, 714-721.
(19) Stolze, K.; Udilova, N.; Nohl, H. *Free Rad. Biol. Med.* 2000, 29, 1005-1014.
(20) Chalier, F.; Tordo, P. *J. Chem. Soc., Perkin Trans.* 2 2002, 2110-2117.
(21) Olive, G.; Mercier, A.; Le Moigne, F.; Rockenbauer, A.; Tordo, P. *Free Rad. Biol. Med.* 2000, 28, 403-408.
(22) Zhang, H.; Joseph, J.; Vasquez-Vivar, J.; Karoui, H.; Nsanzumuhire, C.; Martasek, P.; Tordo, P.; Kalyanaraman, B. *FEBS Lett* 2000, 473, 58-62.
(23) Stolze, K.; Udilova, N.; Nohl, H. *Biol. Chem.* 2002, 383, 813-820.
(24) Stolze, K.; Udilova, N.; Rosenau, T.; Hofinger, A.; Nohl, H. *Biol. Chem.* 2003, 384, 493-500.
(25) Villamena, F.; Zweier, J. *J. Chem. Soc., Perkin Trans.* 2 2002, 1340-1344.
(26) Zhao, H.; Joseph, J.; Zhang, H.; Karoui, H.; Kalyanaraman, B. *Free Rad. Biol. Med.* 2001, 31, 599-606.
(27) Tsai, P.; Ichikawa, K.; Mailer, C.; Pou, S.; Halpern, H. J.; Robinson, B. H.; Nielsen, R.; Rosen, G. M. *J. Org. Chem.* 2003, 68, 7811-7817

The invention claimed is:

1. A compound of formula I:

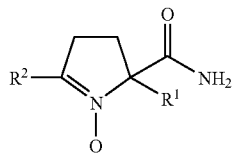

wherein $R^1$ is selected from the group consisting of halo, alkyl, substituted alkyl, branched alkyl, and cyclic alkyl, and $R^2$ is $NH_2$; or a salt thereof.

2. The compound of claim 1 wherein $R^1$ is alkyl.
3. The compound of claim 2 wherein $R^2$ is $NH_2$.
4. The compound of claim 2 wherein $R^1$ is methyl.
5. The compound of claim 4 wherein $R^2$ is $NH_2$.
6. The compound of claim 1 wherein the compound is 2-amino-5-carbamoyl-5-methyl-1-pyrroline N-oxide ($NH_2$-AMPO).
7. A spin trap of formula I:

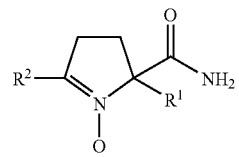

wherein $R^1$ is selected from the group consisting of halo, alkyl, substituted alkyl, branched alkyl, and cyclic alkyl, and $R^2$ is $NH_2$; or a salt thereof.

8. The spin trap of claim 7 wherein $R^1$ is methyl and $R^2$ is $NH_2$.

* * * * *

UNITED STATES PATENT AND TRADEMARK OFFICE
CERTIFICATE OF CORRECTION

PATENT NO. : 7,598,400 B2  Page 1 of 1
APPLICATION NO. : 11/286682
DATED : October 6, 2009
INVENTOR(S) : Villamena et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this

Twenty-eighth Day of September, 2010

David J. Kappos
*Director of the United States Patent and Trademark Office*